(12) United States Patent
Lee et al.

(10) Patent No.: US 9,469,619 B2
(45) Date of Patent: Oct. 18, 2016

(54) METHOD OF PREPARING FURFURAL COMPOUNDS

(71) Applicant: Samsung Electronics Co., Ltd., Suwon-si, Gyeonggi-do (KR)

(72) Inventors: Jong Min Lee, Hwaseong-si (KR); Hyeon Su Heo, Euijeongbu-si (KR); Moo Ho Lee, Suwon-si (KR); Kyung Hae Lee, Incheon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/066,541

(22) Filed: Oct. 29, 2013

(65) Prior Publication Data

US 2014/0128625 A1 May 8, 2014

(30) Foreign Application Priority Data

Oct. 29, 2012 (KR) ........................ 10-2012-0120660
Oct. 28, 2013 (KR) ........................ 10-2013-0128718

(51) Int. Cl.
*C07D 307/46* (2006.01)
*C07D 307/48* (2006.01)
*C07D 307/50* (2006.01)

(52) U.S. Cl.
CPC ........... *C07D 307/46* (2013.01); *C07D 307/48* (2013.01); *C07D 307/50* (2013.01)

(58) Field of Classification Search
CPC .................................................. C07D 307/46
USPC ........................................................ 549/488
See application file for complete search history.

(56) References Cited

U.S. PATENT DOCUMENTS

| 8,115,020 | B2 | 2/2012 | Sanborn |
| 8,231,693 | B2 | 7/2012 | Gruter |
| 8,314,260 | B2 | 11/2012 | Gruter et al. |
| 2010/0004437 | A1 | 1/2010 | Binder et al. |
| 2010/0081833 | A1 | 4/2010 | Gruter et al. |
| 2011/0082304 | A1 | 4/2011 | Gruter et al. |
| 2012/0083610 | A1 | 4/2012 | Gruter et al. |
| 2013/0158254 | A1 | 6/2013 | Binder et al. |

FOREIGN PATENT DOCUMENTS

| EP | 2183236 B1 | 5/2010 |
| WO | WO 2006063220 A2 | 6/2006 |
| WO | WO 2007104514 A2 | 9/2007 |
| WO | WO 2009155297 A1 | 12/2009 |
| WO | WO 2011124639 A1 * | 10/2011 |
| WO | WO 2012091570 A1 | 7/2012 |

OTHER PUBLICATIONS

Van Putten, R., "Hydroxymethylfurfural, a versatile platform chemical made from renewable resources." Chemical reviews 113.3 (2013): 1499-1597.*
Corma, A., "Chemical routes for the transformation of biomass into chemicals." Chemical Reviews 107.6 (2007): 2411-2502.*
Vertex42 LLC, "Periodic Table of the Elements", 2011, p. 1.*
Yang, Y., "Conversion of glucose into furans in the presence of AlCl3 in an ethanol—water solvent system." Bioresource Technology 116 (2012): 190-194.*
Kobayashi et al., "Lewis Acid Catalysts Stable in Water. Correlation between Catalytic Activity in Water and Hydrolysis Constants and Exchange Rate Constants for Substitution of Inner-Sphere Water Ligands", *J. Am. Chem. Soc.*, 120: 8287-8288 (1998).
Pagan-Torrres et al., "Production of 5-Hydroxymethylfurfural from Glucose Using a Combination of Lewis and Bronsted Acid Catalysts in Water in a Biphasis Reactor with an Alkylphenol Solvent", *ACS Catalysis*, 2: 930-934 (2012).
Roman-Leshkor et al., Phase Modifiers Promote Efficient Production of Hydroxymethylfurfural from Fructose, *Science*, (312) 5782:1933-1937 (2006).
Tyrlik et al., "Selective dehydration of glucose to hydroxymethylfufural and a one-pot synthesis of a 4-acetylbutyrolactone from glucose and trioxane in solutions of aluminum salts", *Carbohydrate Research*, 315 (3):268-272 (1999).

* cited by examiner

*Primary Examiner* — Samantha Shterengarts
*Assistant Examiner* — Matt Mauro
(74) *Attorney, Agent, or Firm* — Leydig, Voit & Mayer, Ltd.

(57) ABSTRACT

Provided is a two-step method of producing a compound of chemical formula 1 in the presence of an alcohol solvent and a Group 3B metal catalyst or a salt thereof, comprising a first step comprising alkylation or isomerization of an aldohexose-containing substrate to obtain an intermediate, and a second step comprising dehydration of the intermediate to produce a compound of chemical formula 1. Preferably, additional solvent and/or catalyst are not added in the second step.

15 Claims, No Drawings

METHOD OF PREPARING FURFURAL COMPOUNDS

CROSS-REFERENCE TO RELATED APPLICATIONS

This application claims the benefit of Korean Patent Application No. 10-2012-0120660, filed on Oct. 29, 2012, and Korean Patent Application No. 10-2013-0128718, filed on Oct. 28, 2013 in the Korean Intellectual Property Office, the entire disclosures of which are incorporated herein by reference.

BACKGROUND OF THE INVENTION

1. Field of the Invention

The present invention provides a method of preparing furfural compounds from aldohexose-containing substrate.

2. Description of the Related Art 5-hydroxymethyl-2-furfural (5-HMF), a purine compound that may be derived from renewable biomass, is an intermediate in the production of industrially-important materials. 5-HMF can be converted to 2,5-dimethylfuran (DMF) for liquid biological fuel, and oxidized to 2,5-furandicarboxylic acid (FDCA) for polyester production. Recently, FDCA has been in the limelight as a substituent for terephthalate. In addition, 5-HMF can be converted to an environment-friendly adhesive, cohesive, and coating agent. Thus, there are several studies being done on the mass production of 5-HMF.

The conventional method of producing 5-HMF has used fructose. The fructose of ketohexose can be converted to HMF using only dehydration in the presence of acid catalyst, without requiring an additional isomerization. However, fructose is expensive, and the high boiling point of the solvent used in the conversion requires high energy distillation to be removed. Thus, the 5-HMF production method using fructose has good availability, but cannot be used widely because of its high production cost.

5-HMF can be prepared by thermal dehydration from hexose substrate in the presence of various catalysts in the acidic solution. In this regard, there has been an attempt to develop a chemical synthetic process having a low cost and high yield.

In the disclosure of EP2183236B1, 5-hydroxymethylfurfural was obtained from hexose using an ionic liquid containing an organic cation and an inorganic anion. However, the ionic liquid as a reactant solvent has too a high viscosity to be used in a commercially available process, limited by mass transfer and workability. In addition, impurities in the ionic liquid process has an undesirable effect on the catalytic reaction, and causes some problems in the separation of the reactants and the products.

WO 09/155297 discloses that glucoses is converted to 5-HMF at 81% yield in a polar aprotic solvent. However, the use of organic solvent makes it hard to separate the produced 5-HMF, and thus, the method is difficult to commercialized.

In the prior art, 5-HMF was produced from fructose at a high yield, but from glucose at a very low yield. There is a process of preparing 5-HMF from glucose using various solvents to improve the yield of production from glucose, but it is very complicated process and has a high production cost.

The catalysts used for producing 5-HMP are inorganic acids such as $H_2SO_4$, $H_3PO_4$ and HCl, which are hard to regenerate due to the use of solution. In order to address the regeneration problem, solid sulfuric acid is often used as a catalyst. Because an inactive humin polymer is produced on the surface of a solid acid resin, the solid acid resin is used restrictively.

Therefore, there is a need for a method of efficiently preparing 5-HMF and its derivatives from inexpensive feedstock.

SUMMARY OF THE INVENTION

Provided is a two-step method of producing a compound of chemical formula 1 in the presence of an alcohol solvent and a Group 13 metal catalyst or a salt thereof, comprising a first step comprising alkylation or isomerization of an aldohexose-containing substrate to obtain an intermediate, and a second step comprising dehydration of the intermediate to produce a compound of chemical formula 1. Preferably, additional solvent and/or catalyst are not added in the second step.

DESCRIPTION OF THE PREFERRED EMBODIMENTS

An embodiment of the present invention is to provide a method of producing at least a compound having a chemical formula 1, comprising alkylating and/or isomerizing an aldohexose-containing substrate in the presence of a Group 13 metal catalyst or salt thereof to obtain a reaction product, and dehydrating the reaction product by increasing a reaction temperature to produce a compound of chemical formula 1:

[Chemical Formula 1]

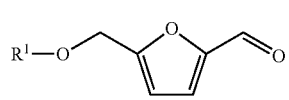

wherein $R^1$ is a hydrogen or a $C_1$-$C_{12}$ alkyl group.

An embodiment provides a method of preparing furfural compounds from aldohexose-containing substrate by performing a two-step reaction using a single catalyst, where a first step is a process of obtaining a reaction product by performing at least a reaction selected from the alkylation and isomerization of an aldohexose-containing substrate; and a second step is a process of performing dehydration of the reaction product obtained in the first step. Using a single catalyst in the first step and the second step, it is possible to achieve increased solubility of the substrate in the solvent through the alkylation of aldohexose-containing substrate and the isomerization of aldohexose. According to the method of the present invention, the conversion rate of aldohexose-containing substrate and the selectivity of HMF and ether compounds thereof can be improved. In addition, because the second step can be performed without adding additional solvent and catalyst, a method of preparing furfural compounds from aldohexose-containing substrate having increased productivity and continuous conversion is provided.

The furfural compounds of the present invention have a chemical formula 1, preferably 5-hydroxymethylfurfural (5-HMF) or an ether compound thereof:

[Chemical Formula 1]

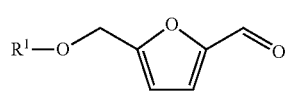

wherein R[1] is a hydrogen, or $C_1$-$C_{12}$ alkyl group. The alkyl group can be linear or branched, and unsubstituted or substituted.

When R[1] is a hydrogen in chemical formula 1, the furfural compound is 5-HMF. When R[1] is an alkyl group, the furfural compound is an ether compound. The alkyl group may include methyl, ethyl, propyl and the like. The ether compounds may include methoxymethylfurfural (MMF), ethoxymethylfurfural (EMF), buthoxymethylfurfural and the like.

According to the method of the present invention, the furfural compound having chemical formula 1 can be obtained from cheap aldohexose-containing substrate at a conversion rate of 97% or higher, and at a selectivity of 20% or higher of 5-HMF and an ether compound thereof having the chemical formula 1.

In the first step, the reaction product can be obtained by performing alkylation and/or isomerization of a substrate in the presence of solvent and catalyst. By performing the first step, it is possible to increase the solubility of aldohexose in the solvent, and to reduce the over-reaction resulting in humin production.

The reaction product obtained after the first step is a resultant product of alkylation and/or isomerization of a substrate, and includes at least one selected from ketohexose, an ether compound of ketohexose and an ether compound of aldohexose. By using the catalyst of the present invention in the first step, high selectivity of the isomerized product can be achieved, for example a selectivity about 50% or higher.

The reaction pressure, temperature and time can be properly controlled depending on the metal in the catalyst and the alcohol. For example, to achieve a high conversion rate, the temperature of first step may be about 50 to 180° C., or preferably about 60 to 130° C., the pressure may be about 1 to 20 atm, or preferably 1 to 5 atm, and reaction time may be about 0.5 to 48 hours or preferably 4 to 36 hours.

The second step produces furfural compounds having chemical formula 1 by performing the dehydration of the reaction product obtained in the first step. Specifically, after the first step, the second step can be initiated by elevating the reaction temperature. In order to determine the hydrating step, the conversion rate of aldohexose-containing substrate in the alkylation and/or isolation step is measured. The second step can begin when the conversion rate of aldohexose-containing substrate is about 10% or higher, or preferably about 30% or higher. The substrate, alcohol and catalyst are added to the reaction before the first step, and additional alcohol and catalyst are preferably not added to the second step.

The reaction product of first step is transparent. In the second step, the transparent reaction product obtained in the first step changes into a non-transparent product due to the production of humin and/or other polymers, thereby blocking the reactor. The reaction product of first step can proceed to the second step without additional alcohol, diluent solvent, and/or catalyst.

However, the second step may be performed by optionally adding alcohol, diluent solvent and/or catalyst, in order to increase the conversion rate of the aldohexose and the selectivity of HMF or an ether thereof. When the alcohol or the diluent solvent is added to the second step, the added amount may be 5 to 50 parts by weight or preferably 10 to 30 parts by weight, based on 100 parts by weight of the alcohol and/or the diluent solvent used in the first step. When the catalyst is added to the second step, the amount is about 3 to 10 parts by weight, based on 100 parts by weight of the catalyst used in the first step. The catalyst or the alcohol may be different from or the same as that used in the first step.

The reaction pressure, temperature and time of the second step can be controlled depending on the metal in the catalyst and the alcohol. For example, the temperature of second step may be about 150 to 280° C., or preferably about 160 to 260° C., the pressure may be about 30 to 80 atm, or preferably 40 to 70 atm, and reaction time may be about 0.1 to 10 minutes or preferably 0.5 to 5 minutes. When the second step is performed under the conditions described above, the production of humin can be minimized to prevent blocking the reactor.

The first step and the second step can be performed in a semi-continuous state or a continuous state.

The substrate includes an aldohexose-containing substrate. Herein, the term "aldohexose-containing substrate" means a substrate comprising saccharides including an aldohexose, for example monosaccharides, disaccharides and polysaccharides; and a mixture of the saccharides and other non-saccharides. If the aldohexose-containing substrate includes saccharide components and non-saccharide components, the amount of saccharides can be 5 to 100 wt % or preferably 30 to 100 wt %, based on the total weight of substrate.

Examples of monosaccharides include allose, altrose, glucose, mannose, idose, galactose and talose. Examples of disaccharides include sucrose, maltose, cellobios, lactose and the like. Examples of polysaccharides include starch, amylose, cellulose, hemi-cellulose, and the like. In an embodiment, the aldohexose-containing substrate contains glucose and/or sucrose. The aldohexose-containing substrate including the saccharide components and non-saccharide components can be obtained from various biomasses.

The catalyst is a metal that belongs to Group 13 of the periodic table, or a salt thereof. Examples of the catalyst include Al (Aluminum), Ga (Gallium), In (Indium), and Tl (Thallium), and salts thereof. The catalyst is preferably Al. The metal can be provided by its salt, such as a sulfate or chloride salt. By using the catalyst, the alkylation of an aldohexose-containing substrate increases solubility in the solvent, and increased isomerization of aldohexose improves the conversion rate of aldohexose-containing substrate and the selectivity of HMF or an ether compound thereof.

The amount of catalyst can be adjusted depending on the reaction rate, and the desired reactivity improvement. For example, the amount of the catalyst can be 0.1 to 50 parts by weight, or preferably 0.5 to 30 parts by weight based on 100 parts by weight of a total amount of saccharide contained in the aldohexose-containing substrate.

The alcohol includes an primary alcohol, a secondary alcohol, and tertiary alcohol containing at least one hydroxyl group, and a mixture thereof. The alcohol can be $C_1$ to $C_{20}$ aliphatic alcohol, or preferably $C_1$-$C_8$ aliphatic alcohol. Examples of the alcohol include at least one selected from the group consisting of methanol, ethanol, n-propanol, i-propanol, n-butanol, i-butanol, iso-butanol, tert-butanol, n-pentanol, n-hexanol, iso-amyl alcohol and iso-octyl alcohol, and preferably at least one selected from the group consisting of methanol, ethanol and a mixture thereof.

The amount of alcohol can be 200 to 2,000 parts by weight, or preferably 500 to 1,000 parts by weight, based on 100 parts by weight of saccharide contained in the aldohexose-containing substrate, in considering the efficient conversion reaction.

In order to facilitate the reaction between the aldohexose-containing substrate and the alcohol, a diluent solvent can be added to the alcohol. Examples of diluent solvent include at least one selected from the group consisting of water; ketones such as acetone, methylethylketone and methylisobutylketone; and sulfoxides such as dimethylsulfoxide (DMSO). The diluent solvent is preferably water.

The diluent solvent may be mixed with the alcohol at an amount of 2 to 50 parts by weight, or preferably 5 to 20 parts by weight, based on 100 parts by weight of the alcohol.

The produced 5-HMF and an ether compounds thereof can be converted to methoxymethyl furfural, ethoxymethyl furfural or butoxymethyl furfural as a commercial solvent, or to 2,5-furandicarboxylic acid (FDCA) for the production of polymers, such as poly(ethylene 2,5-furandicarboxylate, PEF), or other chemicals.

As described above, the present invention provides a method of preparing furfural compounds from aldohexose-containing substrate by performing two step reactions using a single catalyst in the two step reactions, so as to achieve the increased solubility of the substrate to a solvent through an alkylation of aldohexose-containing substrate and the isomerization of aldohexose, resulting in the conversion rate of the aldohexose-containing substrate, and the selectivity of HMF and/or an ether compounds thereof. In addition, the present invention provides a method of preparing furfural compounds from aldohexose-containing substrate by performing the second step without adding an additional catalyst and/or solvent, thereby making it possible to improve the productivity and the continuous process.

A better understanding of the present invention may be obtained through the following examples which are set forth to illustrate, but are not to be construed as limiting the present invention.

Example 1

1-1. Alkylation and Isomerization

In a glass reactor equipped with an agitator for agitating the reactants, a cooler for refluxing an alcohol in the process of alkylation and/or isomerization, a temperature sensor, and a heating mantle for heating the reactants, 30 g of glucose, $AlCl_3.6H_2O$ 2.2 g, 30 g of water, and 270 g of methanol were added and agitated. The reaction temperature was elevated slowly to 80° C., and the solution was refluxed. The reaction was performed at a normal pressure and 80° C. for 5 hours to obtain the reaction product. The reaction product was analyzed with HPLC under the following conditions, and the conversion rate of glucose and the selectivity of alkylated product and isomerized product were calculated. The results are summarized in Table 1.

1-2. Dehydration

In a reaction system equipped with a plug flow reactor, a regulator, a high-pressure liquid pump, and a cooler for cooling the reactants, the reaction product obtained in Example 1-1 were dehydrated by heating at 220° C. and 65 atm, for 5 minutes of retention time. The product was cooled after the dehydration, and analyzed with GC (gas chromatography). The analyzed results are shown in Table 2.

The conditions for HPLC and GC were as follows:
<Gas Chromatography>
Column: Cyclosil-B (30 m, 0.25 mm, 0.25 um)
Inject temperature: 250° C.
Gas flow rate: He 2.5 ml/min,
Oven temperature: 50° C.→20° C./min elevating temperature→250° C. (maintained for 3 minutes)
FID detector temperature: 270° C.
Quantitative analyzing method: internal standard method (standard: tert-Butanol)
<HPLC>
Column: [BIO-RAD] Aminex HPX-87H ion exclusion column
Column temperature: 35° C.
Mobile phase: 0.5 mM $H_2SO_4$ in water
Flow rate: 0.5 ml/min The conversion rate of glucose, selectivity of HMF and an ether compounds thereof, and the yield are calculated as follows.

Conversion rate (%)=(1−(concentration of aldohexose-containing substrate after reaction (g/l)/concentration of aldohexose-containing substrate before reaction (g/L)))*100

Selectivity (%)=(concentrate of HMF or its derivative after reaction (g/L)/concentration of the consumed aldohexose-containing substrate (g/L))*100

Yield (%)=Conversion rate (%)*Selectivity (%)/100

Example 2

This example was performed according to substantially the same method of Example 1, except that the catalyst was 6.5 g of $AlCl_3.6H_2O$. The result was shown in Table 1.

Example 3

This example was performed according to substantially the same method of Example 1, except that the dehydration was performed at a temperature of 240° C. The results are shown in Table 1.

Comparative Example 1

Without performing the step of alkylation and isomerization of glucose of Example 1-1, 30 g of glucose, $AlCl_3.6H_2O$ 2.2 g, 30 g of water, and 270 g of methanol were added to a beaker, agitated at a room temperature to obtain the transparent solution, and then reacted at 220° C. and 65 atm for 5 minutes of retention time. The results are shown in Table 1.

Comparative Examples 2 to 5

These comparative examples were performed according to substantially the same method of Example 1, except that the catalyst was $H_2SO_4$, $SnCl_2.2H_2O$, $FeCl_3.6H_2O$, or $CuCl_2.2H_2O$, instead of $AlCl_3.6H_2O$ as in Example 1. The results are shown in Table 1.

TABLE 1

| Classification | Catalyst | The first step | | | The second step | | | |
| --- | --- | --- | --- | --- | --- | --- | --- | --- |
| | | Selectivity (%) | | Conversion rate (%) | Selectivity (%) | | Conversion rate (%) | Yield (%) |
| | | Methyl glucoside | Fructose & Methylfructoside | | HMF | MMF | | |
| Example 1 | $AlCl_3 \cdot 6H_2O$ | 3.24 | 50.4 | 29.76 | 14.9 | 11.3 | 96.9 | 25.4 |
| Example 2 | $AlCl_3 \cdot 6H_2O$ | 4.02 | 52.8 | 31.56 | 13.9 | 28.7 | 98.4 | 41.9 |
| Example 3 | $AlCl_3 \cdot 6H_2O$ | 3.24 | 50.4 | 29.76 | 12.2 | 10.9 | 98.2 | 22.7 |
| Comp. Example 1 | $AlCl_3 \cdot 6H_2O$ | — | — | — | 6.8 | 11.4 | 96.3 | 17.5 |
| Comp. Example 2 | $H_2SO_4$ | trace | 3.18 | 8.28 | trace | 4.6 | 96.0 | 4.4 |
| Comp. Example 3 | $SnCl_2 \cdot 2H_2O$ | 1.44 | trace | 10.5 | 10.0 | 6.0 | 98.4 | 15.7 |
| Comp. Example 4 | $FeCl_3 \cdot 6H_2O$ | 1.86 | trace | 6.12 | 4.8 | trace | 94.0 | 4.5 |
| Comp. Example 5 | $CuCl_2 \cdot 2H_2O$ | trace | trace | 0.3 | trace | 5.7 | 93.1 | 5.3 |

The Examples using the catalyst of the present invention showed very high production of alkylated product and isomerized product in the first step, compared to the Comparative Examples, and thus provided the high productivity of HMF and the ether compounds thereof in the second step. Thus, according to the present invention, the conversion rate of glucose and the selectivity of HMF and the ether compound thereof were achieved.

As shown in the results of Examples 1 to 3, the yield after the second step was 97% or higher, and the selectivity of the final product was 20% or higher. In the results of the Comparative Examples, the yield after the second step was high, but the selectivity of the final product was very low, such that the methods of the Comparative Examples are not suitable for preparing the furfural compounds.

Example 4

4-1. Alkylation and Isomerization

To the glass reactor which was the same as that of Example 1, 90 g of glucose, $AlCl_3 \cdot 6H_2O$ 6.6 g, 90 g of water, and 630 g of ethanol were added, and agitated. The reaction temperature was elevated slowly to 80° C. where the solution was refluxed. The reaction was performed at a normal pressure at 80° C. for 36 hours to obtain the reaction product. The reaction product was analyzed with HPLC, and the conversion rate of glucose and the selectivity of alkylated product and isomerized product were calculated. The results are summarized in Table 2.

4-2. Dehydration

In the reaction system equipped with a plug flow reactor, regulator, high-pressure liquid pump and a cooler for cooling the reactants, the alkylated product and isomerized product obtained in Example 4-1 were performed for the dehydration reaction at 180° C. and 60 atm, for 3.4 minutes of retention time. The product was cooled after the dehydration, and analyzed with GC (gas chromatography). The results are shown in Table 2.

Example 5

This example was performed according to substantially the same method of Example 1, except that the catalyst was 8.1 g (9 wt %) of $AlCl_3 \cdot 6H_2O$. The results are shown in Table 2.

Example 6

This example was performed according to substantially the same method of Example 4, except that the catalyst was 10 g (11 wt %) of $AlCl_3 \cdot 6H_2O$. The results are shown in Table 2.

Example 7

This example was performed according to substantially the same method of Example 4, except that the dehydration was performed at a temperature of 170° C. The results are shown in Table 2.

Example 8

This example was performed according to substantially the same method of Example 4, except that the dehydration was performed at a temperature of 190° C. The results are shown in Table 2.

Example 9

This example was performed according to substantially the same method of Example 4, except that sucrose was used as a starting material, instead of glucose. The results are shown in Table 2.

TABLE 2

| Classification | The first step | | | The second step | | | |
| --- | --- | --- | --- | --- | --- | --- | --- |
| | Selectivity (%) | | Conversion rate (%) | Selectivity (%) | | Conversion rate (%) | Yield (%) |
| | Ethyl-glucoside/ fructoside | Fructose | | HMF | EMF | | |
| Example 4 | 90 | 10 | 85.1 | 30.7 | 18.7 | 97.7 | 48.3 |
| Example 5 | 75 | 25 | 73.6 | 21 | 15 | 97.1 | 35.0 |
| Example 6 | 73 | 27 | 68.1 | 24 | 30 | 98.3 | 53.1 |
| Example 7 | 90 | 10 | 85.1 | 30.1 | 14.4 | 95.5 | 42.5 |
| Example 8 | 90 | 10 | 85.1 | 32.2 | 14.8 | 98.4 | 46.2 |
| Example 9 | 85 | 30 | 88.3 | 38.2 | 16.8 | 98.3 | 54.1 |

The Examples using ethanol as an alcohol component showed better results for alkylated product and isomerized product in the first step than those using methanol, and provided high productivity of HMF and the ether compounds thereof in the second step. In addition, Example 9 showed that the yield of product obtained from sucrose was higher than glucose as a starting material.

What is claimed is:

1. A method of producing a compound of chemical formula 1, comprising
    alkylating and isomerizing an aldohexose-containing substrate in the presence of a Group 13 metal catalyst or salt thereof and a $C_1$-$C_{12}$ alcohol at a temperature of 60° C. to 130° C. and at a pressure of 1 atm to 20 atm to obtain a reaction product, and
    dehydrating the reaction product at a temperature of 160° C. to 260° C. and at a pressure of 30 atm to 80 atm without adding an additional catalyst and/or alcohol to produce a compound of chemical formula 1:

[Chemical Formula 1]

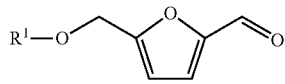

wherein R1 is a hydrogen or a C1-C12 alkyl group.

2. The method of claim 1, wherein the alkylating and isomerizing step is performed for 0.5 to 48 hours, and the second step is performed for 0.1 to 10 hours.

3. The method of claim 1, wherein the dehydrating step is initiated when the conversion rate of aldohexose-containing substrate in the alkylating and isomerizing step is 10% or higher.

4. The method of claim 1, wherein the metal of the catalyst is selected from the group consisting of Al, Ga, In, and Tl.

5. The method of claim 1, wherein the amount of catalyst is 0.1 to 50 parts by weight per 100 parts by weight of saccharide contained in the aldohexose-containing substrate.

6. The method of claim 1, wherein aldohexose-containing substrate comprises at least one saccharide selected from the group consisting of allose, altrose, glucose, mannose, idose, galactose, talose, sucrose, maltose, cellobios, lactose, starch, amylose, cellulose, and hemi-cellulose.

7. The method of claim 1, wherein the alkylating and/or isomerizing step is performed in the presence of alcohol, and the alcohol comprises at least one selected from the group consisting of methanol, ethanol, n-propanol, i-propanol, n-butanol, i-butanol, iso-butanol, tert-butanol, n-pentanol, n-hexanol, iso-amyl alcohol, and iso-octyl alcohol.

8. The method of claim 7, wherein the amount of alcohol is 200 to 2000 parts by weight per 100 parts by weight of saccharide contained in the aldohexose-containing substrate.

9. The method of claim 7, wherein at least a diluent solvent is mixed with the alcohol at an amount of 2 to 50 parts by weight per 100 parts by weight of the alcohol.

10. The method of claim 9, wherein the diluent solvent is selected from the group consisting of water, acetone, methylethylketone, methylisobutylketone, and dimethylsulfoxide.

11. The method of claim 1, wherein the reaction product comprises a ketohexose, an ether compound of ketohexose, or an ether compound of aldohexose.

12. The method of claim 1, wherein the conversion rate of the aldohexose after the second step is 97% or higher, and the selectivity of at least one hydroxymethylfurfural (HMF) or ether compound thereof represented by chemical formula 1 is 20% or higher.

13. The method of claim 1, wherein the compound of chemical formula 1 is 5-hydroxymethyl-2-furfural (5-HMF).

14. The method of claim 1, wherein alkylating and isomerizing the aldohexose-containing substrate comprises heating the aldohexose-containing substrate to a temperature of 60° C. to 130° C. at a pressure of 1 to 20 atm for a period of 0.5 to 48 hours.

15. The method of claim 1, wherein dehydrating the reaction intermediate product comprises heating the reaction product intermediate to a temperature of 160° C. to 260° C. at a pressure of 30 to 80 atm for a period of 0.1 to 10 hours.

* * * * *